United States Patent
Santarelli et al.

(10) Patent No.: US 8,846,942 B2
(45) Date of Patent: Sep. 30, 2014

(54) LUMINESCENT SOLAR CONCENTRATOR COMPRISING DISUBSTITUTED BENZOTHIADIAZOLE COMPOUNDS

(75) Inventors: Samuele Santarelli, Novara (IT); Roberto Fusco, Novara (IT); Gabriele Bianchi, Novara (IT)

(73) Assignee: Eni S.p.A., Rome (IT)

( * ) Notice: Subject to any disclaimer, the term of this patent is extended or adjusted under 35 U.S.C. 154(b) by 0 days.

(21) Appl. No.: 13/569,840

(22) Filed: Aug. 8, 2012

(65) Prior Publication Data

US 2013/0204007 A1    Aug. 8, 2013

(30) Foreign Application Priority Data

Aug. 8, 2011 (IT) ............... MI2011A1520

(51) Int. Cl.
| | | |
|---|---|---|
| C07D 417/14 | (2006.01) | |
| C08G 61/12 | (2006.01) | |
| H01L 51/00 | (2006.01) | |
| H01L 31/055 | (2014.01) | |
| C08G 73/08 | (2006.01) | |
| C09K 11/06 | (2006.01) | |
| H05B 33/10 | (2006.01) | |

(52) U.S. Cl.
CPC .... *H01L 51/0032* (2013.01); *C09K 2211/1092* (2013.01); *C08G 61/126* (2013.01); *Y02E 10/52* (2013.01); *C08G 2261/90* (2013.01); *C09K 2211/1011* (2013.01); *C09K 2211/1051* (2013.01); *H01L 31/055* (2013.01); *C08G 73/08* (2013.01); *C08G 61/123* (2013.01); *C09K 11/06* (2013.01); *C08G 2261/414* (2013.01); *H05B 33/10* (2013.01); *C08G 2261/3223* (2013.01); *C09K 2211/1007* (2013.01); *C08G 2261/226* (2013.01); *C08G 2261/3246* (2013.01); *C07D 417/14* (2013.01)
USPC ...................................................... 548/126

(58) Field of Classification Search
None
See application file for complete search history.

(56) References Cited

U.S. PATENT DOCUMENTS

2006/0063027 A1 * 3/2006 Vestweber et al. ............ 428/690

FOREIGN PATENT DOCUMENTS

WO    WO2012007834    *    1/2012

OTHER PUBLICATIONS

Kong et al., A benzothiadiazole-based oligothiophene for vacuum-deposited organic photovoltaic cells. Solar Energy Materials & Solar Cells 2010, 94, 2057-2063.*
Rowan et al., Advanced Material Concepts for Luminescent Solar Concentrators. IEEE Journal of Selected Topics in Quantum Electronics 2008, 14, 1312-1322.*
Wang et al., Performance of Organic Luminescent Solar Concentrator Photovoltaic Systems. AIP Conference Proceedings 2011, 1407, 163-167.*
Sun et al., Benzothiadiazole-sandwiched quarter thiophene-based oligomer for organic solar cells. Synthetic Metals 2009, 159, 556-560.*
van Stark et al., Luminescent Solar Concentrators—A review of recent results. Optic Express 2008, 16, 21773-21792.*
Wang et al., Donor Polymers Containing Benzothiadiazole and Four Thiophene Rings in Their Repeating Units with Improved Photovoltaic Performance. Macromolecules 2009, 42, 4410-4415.*
Beaujuge et al., Green Dioxythiophene-Benzothiadiazole Donor—Acceptor Copolymers for Photovoltaic Device Applications. Chemistry of Materials 2010, 22, 2093-2106.*
Biniek et al., Electronic Properties and Photovoltaic Performance of a Series of Oligothiophene Copolymers Incorporating Both Thieno[3,2-b]thiophene and 2,1,3-Benzothiadiazole Moieties. Macromolecular Rapid Communications 2010, 31, 651-656 (supplemental information included).*

* cited by examiner

*Primary Examiner* — Michael Barker
*Assistant Examiner* — Po-Chih Chen
(74) *Attorney, Agent, or Firm* — Tarolli, Sundheim, Covell & Tummino LLP

(57) ABSTRACT

Luminescent solar concentrator (LSC) includes at least one disubstituted benzothiadiazole compound having general formula (I):

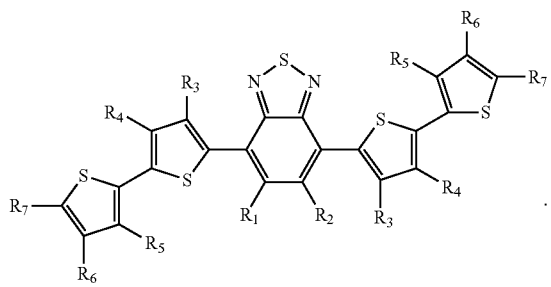

(I)

4 Claims, 3 Drawing Sheets

LUMINESCENT SOLAR CONCENTRATOR COMPRISING DISUBSTITUTED BENZOTHIADIAZOLE COMPOUNDS

RELATED APPLICATION

This application claims priority to Italian Application No. MI2011A001520, filed Aug. 8, 2011, the subject matter of which is incorporated herein by reference in its entirety.

BACKGROUND

It is known that single-junction photovoltaic cells are not capable of efficiently exploiting all the solar radiation. Their efficiency, in fact, is maximum only within a certain spectrum range which comprises a part of visible radiation and a part of infrared radiation.

Spectrum converter materials capable of capturing solar radiation outside the optimal spectral range and og converting it to effective radiation, can be used for enhancing the performance of photovoltaic cells. Furthermore, luminescent solar concentrators (LSC) can be produced with these materials, which allow a further increase in the production of current of photovoltaic cells.

Said luminescent solar concentrators (LSC) generally consist of large sheets of material transparent to solar radiation, in which fluorescent substances are dispersed, or chemically bound to said material, which act as spectrum converters. Due to the effect of the optical phenomenon of total reflection, the radiation emitted by the fluorescent molecules is "driven" towards the thin edges of the sheet where it is concentrated on photovoltaic cells or solar cells positioned therein. In this way, large surfaces of low-cost materials (photoluminescent sheets) can be used for concentrating the light on small surfaces of high-cost materials (photovoltaic cells or solar cells).

A fluorescent compound should have numerous characteristics for being advantageously used in the construction of luminescent solar concentrators (LSC) and these are not always mutually compatible.

First of all, the frequency of the radiation emitted by fluorescence must correspond to an energy higher than the threshold value below which the semiconductor, representing the core of the photovoltaic cell, is no longer able to work.

Secondly, the absorption spectrum of the fluorescent compound should be as extensive as possible, so as to absorb most of the including solar radiation and then to re-emit it at the desired frequency.

It is also desirable that the absorption of the solar radiation be extremely intense, so that the fluorescent compound can exert its function at the lowest possible concentrations, avoiding the use of huge quantities.

Furthermore, the absorption process of solar radiation and its subsequent re-emission at lower frequencies, must take place with the highest possible efficiency, minimizing the so-called non-radiative losses, often collectively indicated with the term "thermalization": the efficiency of the process is measured by its quantum yield.

Finally, the absorption and emission frequencies must be as diverse as possible, as, otherwise, the radiation emitted by a molecule of the fluorescent compound would be absorbed and at least partially diffused by the adjacent molecules. This phenomenon, normally called self-absorption, inevitably leads to a significant loss in efficiency. The difference between the frequencies of the peak with the lower frequency of the absorption spectrum and the peak of the radiation emitted, is normally indicated as Stokes shift and measured as nm (it is not the difference between the two frequencies that is measured, but the difference between the two wavelengths which correspond to them). High Stokes shifts are absolutely necessary for obtaining high efficiencies of luminescent solar concentrators (LSC), bearing in mind the already mentioned necessity that the frequency of the radiation emitted corresponds to an energy higher than the threshold value below which the photovoltaic cell cannot function.

It is known that some benzothiadiazole compounds, in particular 4,7-di(thien-2'-yl)-2,1,3-benzothiadiazole (DTB), are fluorescent compounds which can be used in the construction of luminescent solar concentrators (LSC). Compounds of this type are described in Italian patent application MI 2009 A 001796 in the name of the Applicant.

4,7-di(thien-2'-yl)-2,1,3-benzothiadiazole (DTB) is characterized by an emission centred around 579 nm, which corresponds to an energy well above the minimum threshold value for the functioning of photovoltaic cells, said threshold corresponding for example to a wavelength of about 1100 nm for the most widely-used cells, based on silicon. Furthermore, its absorption of the light radiation is intense and extends over a relatively wide range of wavelengths, indicatively ranging from 550 nm (green radiation wavelength) to ultraviolet. Finally, 4,7-di(thien-2'-yl)-2,1,3-benzothiadiazole (DTB) has a Stokes shift in dichloromethane solution, equal to 133 nm, well above that of most of the commercial products so far proposed for use in luminescent solar concentrators.

For these reasons, the use of 4,7-di(thien-2'-yl)-2,1,3-benzothiadiazole (DTB) has enabled the production of high-quality luminescent solar concentrators (LSC).

Although 4,7-di(thien-2'-yl)-2,1,3-benzothiadi-azole (DTB) absorbs a significant part of the solar spectrum, however, it has a modest absorption in its higher wavelength regions, corresponding to yellow and red radiations which cannot therefore be converted into other radiations more effectively exploited by the photovoltaic cell. For this reason, it is desirable to avail of fluorescent compounds having a more red-shifted absorption spectrum.

The Applicant has therefore considered the problem of finding compounds having a more red-shifted absorption spectrum.

SUMMARY

The present invention relates to a luminescent solar concentrator (LSC) comprising at least one disubstituted benzothiadiazole compound.

The present invention also relates to the use of at least one disubstituted benzothiadiazole compound in the construction of luminescent solar concentrators (LSC).

The present invention also relates to a photovoltaic device selected, for example, from photovoltaic cells, photovoltaic modules, solar cells, solar modules, on both rigid and flexible support, comprising a luminescent solar concentrator (LSC) including at least one disubstituted benzothiadiazole compound.

DETAILED DESCRIPTION

Figure 1:
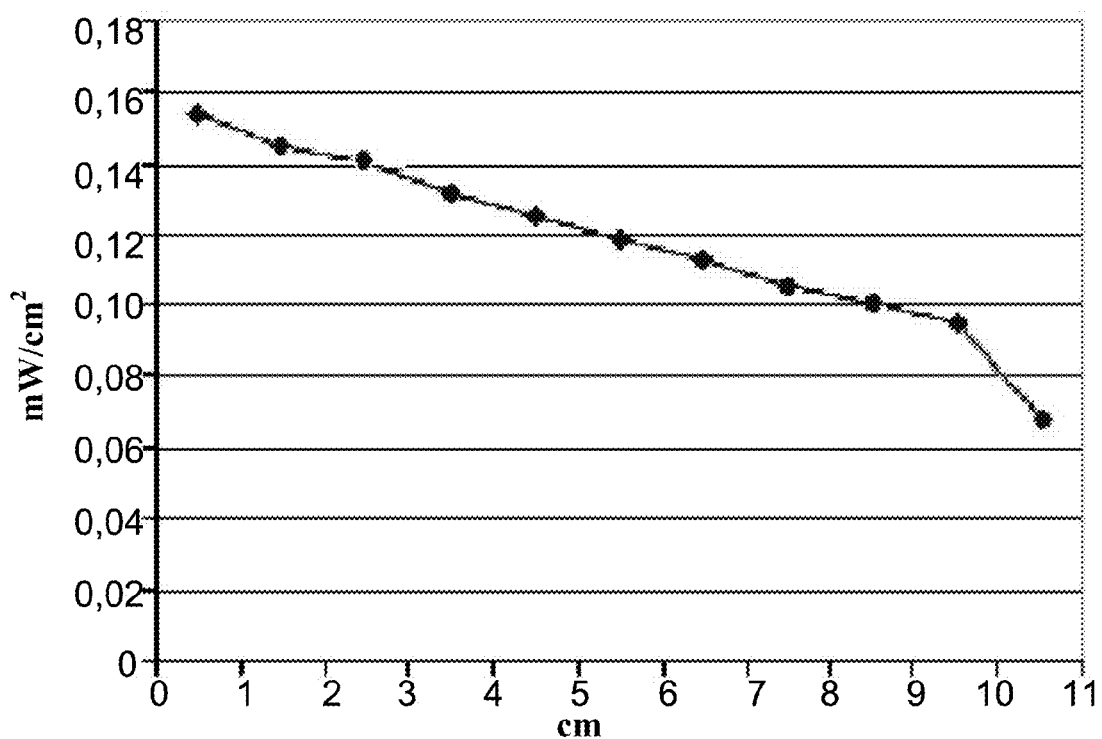
FIG. 1 illustrates the curve relating to the value of the power generated per unit of surface illuminated, expressed as $mW/cm^2$, in relation to the distance of the cover from the edge of the support containing the solar cell.

The Applicant has now found that disubstituted benzothiadiazole compounds having a specific general formula (i.e. having general formula (I) indicated hereunder), can be advantageously used in the construction of luminescent solar concentrators (LSC).

Said luminescent solar concentrators (LSC) can be advantageously used in the construction of photovoltaic devices such as, for example, photovoltaic cells, photovoltaic modules, solar cells, solar modules, on both rigid and flexible supports. Said disubstituted benzothiadiazole compounds, in fact, have a much more red-shifted absorption spectrum with respect to known benzothiadiazole compounds.

Furthermore, said disubstituted benzothiadiazole compounds have higher Stokes shifts than those of the known benzothiadiazole compounds.

An object of the present invention therefore relates to a luminescent solar concentrator (LSC) comprising at least one disubstituted benzothiadiazole compound having general formula (I):

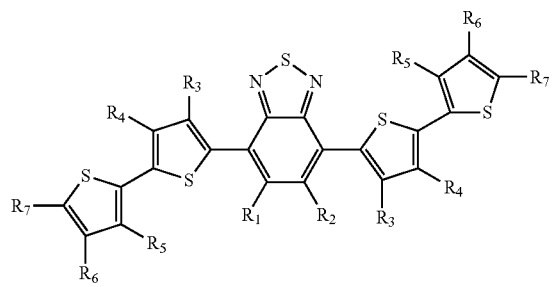

(I)

wherein:
$R_1$, $R_2$, $R_3$, $R_4$, $R_5$, $R_6$ and $R_7$, equal to or different from each other, represent a hydrogen atom; or they are selected from linear or branched $C_1$-$C_{20}$, preferably $C_1$-$C_{10}$, alkyl groups, cycloalkyl groups optionally substituted, aryl groups optionally substituted, linear or branched $C_1$-$C_{20}$, preferably $C_1$-$C_{10}$, alkoxyl groups, optionally substituted;

or $R_1$ and $R_2$, can be optionally bound to each other so as to form, together with the carbon atoms to which they are bound, a cycle or a polycyclic system containing from 3 to 14 carbon atoms, preferably from 4 to 6 carbon atoms, saturated, unsaturated, or aromatic, optionally containing one or more heteroatoms such as, for example, oxygen, sulfur, nitrogen, silicon, phosphorous, selenium;

or $R_3$ and $R_4$, can be optionally bound to each other so as to form, together with the carbon atoms to which they are bound, a cycle or a polycyclic system containing from 3 to 14 carbon atoms, preferably from 4 to 6 carbon atoms, saturated, unsaturated, or aromatic, optionally containing one or more heteroatoms such as, for example, oxygen, sulfur, nitrogen, silicon, phosphorous, selenium;

or $R_5$ and $R_6$, can be optionally bound to each other so as to form, together with the carbon atoms to which they are bound, a cycle or a polycyclic system containing from 3 to 14 carbon atoms, preferably from 4 to 6 carbon atoms, saturated, unsaturated, or aromatic, optionally containing one or more heteroatoms such as, for example, oxygen, sulfur, nitrogen, silicon, phosphorous, selenium;

or $R_6$ and $R_7$, can be optionally bound to each other so as to form, together with the carbon atoms to which they are bound, a cycle or a polycyclic system containing from 3 to 14 carbon atoms, preferably from 4 to 6 carbon atoms, saturated, unsaturated, or aromatic, optionally containing one or more heteroatoms such as, for example, oxygen, sulfur, nitrogen, silicon, phosphorous, selenium.

According to a preferred embodiment of the present invention, in said general formula (I), the substituents $R_1$, $R_2$, $R_3$, $R_4$, $R_5$, $R_6$ and $R_7$, represent a hydrogen atom.

A particularly preferred aspect of the present invention therefore relates to a luminescent solar concentrator (LSC) comprising 4,7-di(2',2"-bi-thien-5'-yl)-2,1,3-benzothiadiazole (QTB) having formula (Ia):

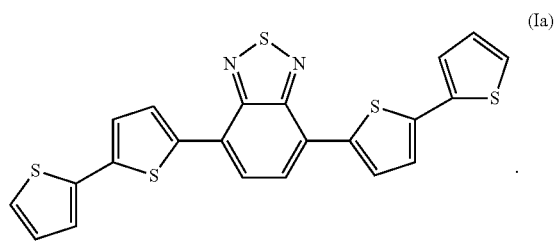 [SMILES: c1csc(-c2ccc(-c3ccc(-c4ccc(-c5cccs5)s4)c4nsnc34)s2)c1]

(Ia)

According to a further preferred embodiment of the present invention, in said general formula (I), the substituents $R_1$, $R_2$, $R_3$, $R_4$, $R_5$ and $R_6$, represent a hydrogen atom, the substituent $R_7$ represents a hexyl group.

A particularly preferred aspect of the present invention therefore relates to a luminescent solar concentrator (LSC) comprising 4,7-di(5"-n-hexyl-2',2"-bithien-5'-yl)-2,1,3-benzothiadiazole (QTB-ex) having formula (Ib):

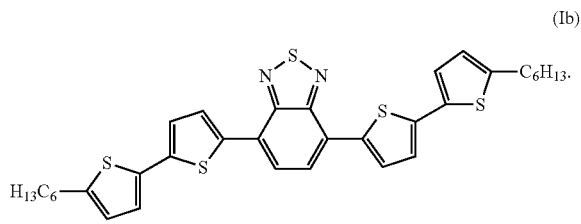

(Ib)

As indicated above, the benzothiadiazole compound having general formula (I) has an absorption, with respect to that of 4,7-di(thien-2'-yl)-2,1,3-benzothia diazole (DTB), which is more red-shifted: this absorption is intense and extensive over a relatively wide wavelength range which, for example, for both 4,7-di(2',2"-bi-thien-5'-yl)-2,1,3-benzothiadiazole (QTB) having formula (Ia) and for 4,7-di-(5"-n-hexyl-2',2"-bithien-5'-yl)-2,1,3-benzothia-diazole (QTB-ex) having formula (Ib), ranges from 230 nm to 590 nm. Furthermore, said compound having general formula (I) has a particularly high Stokes shift. 4,7-di(2',2"-bi-thien-5'-yl)-2,1,3-benzothiadiazole (QTB) having formula (Ia), for example, has a Stokes shift, in dichloromethane solution, equal to 158 nm, whereas 4,7-di(5"-n-hexyl-2',2"-bithien-5'-yl)-2,1,3-benzo-thiadiazole (QTB-ex) having formula (Ib), has a Stokes shift, in dichloromethane solution, equal to 166 nm: consequently, higher Stokes shifts than that, already high, of 4,7-di(thien-2'-yl)-2,1,3-benzothiadiazole (DTB).

For the purpose of the present description and of the following claims, the definitions of the numerical ranges always comprise the extremes unless otherwise specified.

The term "$C_1$-$C_{20}$ alkyl groups" refers to linear or branched alkyl groups having from 1 to 20 carbon atoms. Specific examples of $C_1$-$C_{20}$ alkyl groups are: methyl, ethyl, n-propyl, iso-propyl, n-butyl, iso-butyl, t-butyl, pentyl, ethyl-hexyl, hexyl, heptyl, octyl, nonyl, decyl, dodecyl.

The term "cycloalkyl groups" refers to cycloalkyl groups having from 3 to 10 carbon atoms. Said cycloalkyl groups can be optionally substituted with one or more groups, equal to or different from each other, selected from: halogen atoms such as, for example, fluorine, chlorine, preferably fluorine; hydroxyl groups; $C_1$-$C_{20}$ alkyl groups; $C_1$-$C_{20}$ alkoxyl groups; cyano groups; amino groups; nitro groups; aryl groups. Specific examples of cycloalkyl groups are: cyclopropyl, 1,4-dioxine, 2,2-difluorocyclopropyl, cyclobutyl, cyclopentyl, cyclohexyl, methylcyclohexyl, methoxycyclohexyl, fluorocyclohexyl, phenylcyclohexyl.

The term "aryl groups" means aromatic carbocyclic groups. Said aryl groups can be optionally substituted with one or more groups, equal to or different from each other, selected from: halogen atoms such as, for example, fluorine, chlorine, preferably fluorine; hydroxyl groups; $C_1$-$C_{20}$ alkyl groups; $C_1$-$C_{20}$ alkoxyl groups; cyano groups; amino groups; nitro groups; aryl groups. Specific examples of aryl groups are: phenyl, methylphenyl, trimethylphenyl, methoxyphenyl, hydroxyphenyl, phenyloxyphenyl, fluorophenyl, pentafluorophenyl, chlorophenyl, nitrophenyl, dimethylamminophenyl, naphthyl, phenylnaphthyl, phenanthrene, anthracene.

The term "$C_1$-$C_{20}$ alkoxyl groups" refers to linear or branched alkoxyl groups having from 1 to 20 carbon atoms. Said alkoxyl groups can be optionally substituted with one or more groups, equal to or different from each other, selected from: halogen atoms such as, for example, fluorine, chlorine, preferably fluorine; hydroxyl groups; $C_1$-$C_{20}$ alkyl groups; $C_1$-$C_{20}$ alkoxyl groups; cyano groups; amino groups; nitro groups. Specific examples of $C_1$-$C_{20}$ alkoxyl groups are: methoxyl, ethoxyl, fluoroethoxyl, n-propoxyl, iso-propoxyl, n-butoxyl, n-fluoro-butoxyl, iso-butoxyl, t-butoxyl, pentoxyl, hexyloxyl, heptyloxyl, octyloxyl, nonyloxyl, decyloxyl, dodecyloxyl.

The term "cyclo or polycyclic system" relates to a system containing one or more rings containing from 3 to 14 carbon atoms, optionally containing heteroatoms selected from nitrogen, oxygen, sulfur, silicon, selenium, phosphorous. Specific examples of cyclo or polycyclic system are: thieno[3,2-b]thiophene, thiadiazole, benzothiophene, quinoxaline, pyridine.

Said compound having general formula (I) can be obtained according to processes known in the art as described, for example, in: "Organic Letters" (2011), Vol. 13, pages 90-93; "Chemistry—A European Journal" (1998), Vol. 4, pages 1235-1243; "Chemistry—A European Journal" (2007), Vol. 13, pages 10046-10054, "Journal of Materials Chemistry" (2009), Vol. 19, pages 7730-7737.

Said compound having general formula (I) can be obtained, for example, as indicated in the following scheme:

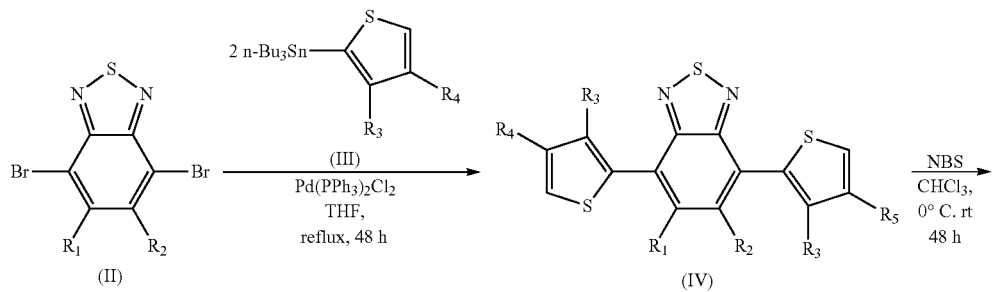

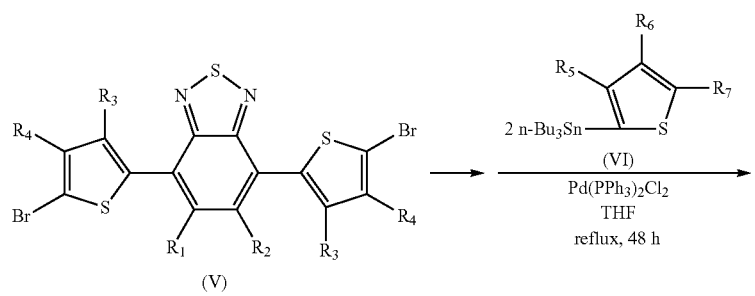

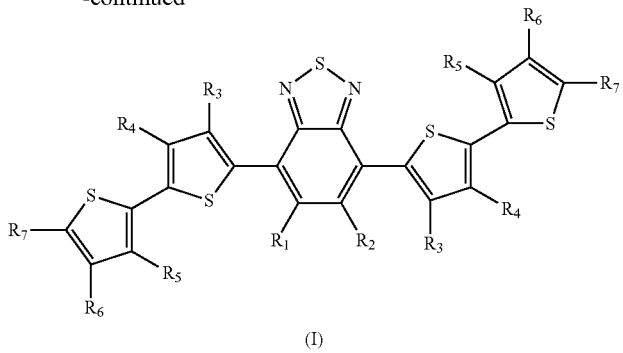

(I)

wherein $R_1$, $R_2$, $R_3$, $R_4$, $R_5$, $R_6$ and $R_7$, have the same meanings defined above, $Pd(PPh_3)_2Cl_2$ is palladium dichlorotriphenylphosphine, THF is tetrahydrofuran, NBS is N-bromosuccinimide, $CHCl_3$ is chloroform, rt indicates room temperature (25° C.).

The benzothiadiazole compound having general formula (II) can be obtained according to processes known in the art, for example, by halogenation of the corresponding benzothiadiazole compounds. Further details relating to these processes can be found, for example, in: "Tetrahedron" (2005), Vol. 61, pages 7453-7460; "European Journal of Organic Chemistry" (2006), pages 4924-4933.

The tri-n-butyl(thien-2-yl)stannane having general formula (III) and the tri-n-butyl(thien-2-yl)stannane having general formula (VI), can be obtained according to processes known in the art such as, for example, by lithiation and subsequent stannylation of the corresponding thiophene compounds. Further details relating to these processes can be found, for example, in: "Journal of the Chemical Society, Perkin Transactions 1: Organic and Bio-Organic Chemistry" (1988), pages 2415-2422; "Journal of Polymer Science, Part A: Polymer Chemistry" (2010), Vol. 48, pages 1714-1720. In particular, tri-n-butyl(thien-2-yl)stannane having general formula (III), wherein $R_3$ and $R_4$, are hydrogen atoms, can be easily found on the market.

A further object of the present invention relates to the use of at least one disubstituted benzothiadiazole compound having general formula (I) in the construction of luminescent solar concentrators (LSC).

The benzothiadiazole compound having general formula (I) can be used in said luminescent solar concentrator (LSC) in the following forms: dispersed in the polymer or in glass, chemically bound to the polymer or glass, in solution, in gel form.

The luminescent solar concentrator (LSC) can contain, for example, a transparent matrix, wherein the term "transparent matrix" refers to any transparent material used in the form of a carrier, ligand, or a material in which at least one disubstituted benzothiadiazole compound having general formula (I) is dispersed or englobed. The material used for the matrix is transparent, as such, to the radiations of interest and, in particular, to radiations having a frequency within the effective spectrum of the photovoltaic device (e.g., the photovoltaic cell) in which it is used. Materials suitable for the purpose of the present invention can therefore be selected from materials transparent to at least radiations having a wavelength ranging from 250 nm to 1100 nm.

The transparent matrix that can be used for the purpose of the present invention can be selected, for example, from polymeric or vitreous materials. Said matrix is characterized by a high transparency and a high duration with respect to heat and light. Polymeric materials which can be advantageously used for the purpose of the present invention are, for example, polymethylmethacrylate (PMMA), epoxy resins, silicon resins, polyalkylene terephthalates, polycarbonates, polystyrene, polypropylene. Vitreous materials which can be advantageously used for the purposes of the present invention are, for example, silicas.

If the matrix is of the polymeric type, said at least one disubstituted benzothiadiazole compound having general formula (I) can be dispersed in the polymer of said matrix by means, for example, of melt dispersion, and subsequent formation of a sheet comprising said polymer and said at least one disubstituted benzothiadiazole compound having general formula (I), operating, for example, according to the technique known as casting. Alternatively, said at least one disubstituted benzothiadiazole compound having general formula (I) and the polymer of said matrix can be solubilized in at least one solvent obtaining a solution which is deposited on a sheet of said polymer, forming a film comprising said at least one disubstituted benzothiadiazole compound having general formula (I) and said polymer, operating, for example, with the use of a Doctor Blade-type film applicator: said solvent is subsequently left to evaporate.

If the matrix is of the vitreous type, said at least one disubstituted benzothiadiazole compound having general formula (I) can be solubilized in at least one solvent obtaining a solution which is deposited on a sheet of said matrix of the vitreous type, forming a film comprising said at least one disubstituted benzothiadiazole compound having general formula (I), operating, for example, with the use of a Doctor Blade-type film applicator: said solvent is subsequently left to evaporate.

A further object of the present invention also relates to a photovoltaic device selected from photovoltaic cells, photovoltaic modules, solar cells, solar modules, on both rigid and flexible supports, comprising a luminescent solar concentrator (LSC) including at least one disubstituted benzothiadiazole compound having general formula (I).

Said photovoltaic device can be obtained, for example, by assembling the above luminescent solar concentrator with a photovoltaic cell.

According to a preferred embodiment of the present invention, the above solar concentrator can be produced in the form of a transparent sheet obtained through the solubilization of said at least one disubstituted benzothiadiazole compound having general formula (I) and of the polymer of the matrix of the polymeric type, in at least one solvent, obtaining a solution which is deposited on a sheet of said polymer forming a film comprising said at least one disubstituted benzothiadiazole compound having general formula (I) and said polymer, operating, for example, with the use of a Doctor Blade-type film applicator: said solvent is subsequently left to evaporate. In said solar devices, said sheets can then be coupled with a photovoltaic cell.

Some illustrative and non-limiting examples are provided hereunder for a better understanding of the present invention and for its embodiment.

4,7-Di(2',2"-bithien-5'-yl)-2,1,3-benzothiadi-azole (QTB) having formula (Ia) was obtained as described in "Organic Letters" (2011), Vol. 13, pages 90-93; whereas 4,7-di(5"-n-hexyl-2',2"-bithien-5'-yl)-2,1,3-benzothiadiazole (QTB-ex) having formula (Ib) was obtained as described in "Chemistry—A European Journal" (2007), Vol. 13, pages 10046-10054.

4,7-Di(thien-2'-yl)-2,1,3-benzothiadiazole (DTB) was obtained as described in patent application MI 2010 A 001316 in the name of the Applicant, whose content is incorporated herein as reference.

EXAMPLE 1

6 g of polymethylmethacrylate Altuglas VSUVT 100 (PMMA) and 76.5 mg of 4,7-di(2',2"-bithien-5'-yl)-2,1,3-benzothiadiazole (QTB), were dissolved in 30 ml of 1,2-dichlorobenzene. The solution obtained was subsequently uniformly deposited on a polymethylmethacrylate sheet Altuglas VSUVT 100 (PMMA) (dimensions 90×90×6 mm) using a Doctor Blade-type film applicator and the solvent was left to evaporate at room temperature (25° C.), in a light stream of air, for 24 hours. A red-coloured transparent sheet was obtained (sheet 1), the colour being conferred by the film, whose thickness proved to range from 300 μm to 350 μm.

A photovoltaic cell IXYS-XOD17, having a surface of 1.2 cm$^2$ was then applied to one of the edges of the polymeric sheet.

The main side of the polymeric sheet [that covered by the thin film containing 4,7-di(2',2"-bithien-5'-yl)-2,1,3-benzothiadiazole (QTB)] was then illuminated, with a light source having a power of 1 sun (1000 W/m$^2$) and the electric power generated by the illumination was measured.

The power measurements were carried out by covering, with an opaque coating (cover), surfaces having variable areas of the polymeric support, at an increasing distance from the edge on which the photovoltaic cells were fixed. These measurements under variable screening conditions allow to quantify the contribution of possible waveguide, edge or multiple diffusion effects due to the support and consequently to be subtracted.

It can be seen that, in the absence of edge effects, the average power generated is equal to 0.12 W/cm$^2$ (FIG. 1).

EXAMPLE 2

6 g di polymethylmethacrylate Altuglas VSUVT 100 (PMMA) and 104.2 mg of 4,7-di(5"-n-hexyl-2',2"-bithien-5'-yl)-2,1,3-benzothiadiazoloe (QTB-ex) were dissolved in 30 ml of 1,2-dichlorobenzene. The solution obtained was then uniformly deposited on a sheet of polymethylmethacrylate Altuglas VSUVT 100 (PMMA) (dimensions 90×90×6 mm)) using a Doctor Blade-type film applicator and the solvent was left to evaporate at room temperature (25° C.), in a light stream of air, for 24 hours. A red-coloured transparent sheet was obtained (sheet 1), the colour being conferred by the film, whose thickness proved to range from 300 μm to 350 μm.

A photovoltaic cell IXYS-XOD17, having a surface of 1.2 cm$^2$ was then applied to one of the edges of the polymeric sheet.

The main side of the polymeric sheet (that covered with the thin film containing 4,7-di(5"-n-hexyl-2',2"-bithien-5'-yl)-2,1,3-benzothiadiazole (QTB-ex)) was then illuminated with a light source having a power of 1 sun (1000 W/m$^2$) and the electric power generated by the effect of the illumination was measured.

The power measurements were carried out by covering, with an opaque coating (cover), surfaces having variable areas of the polymeric support, at an increasing distance from the edge on which the photovoltaic cells were fixed. These measurements under variable screening conditions allow to quantify the contribution of possible waveguide, edge or multiple diffusion effects due to the support and consequently to be subtracted.

Figure 2:
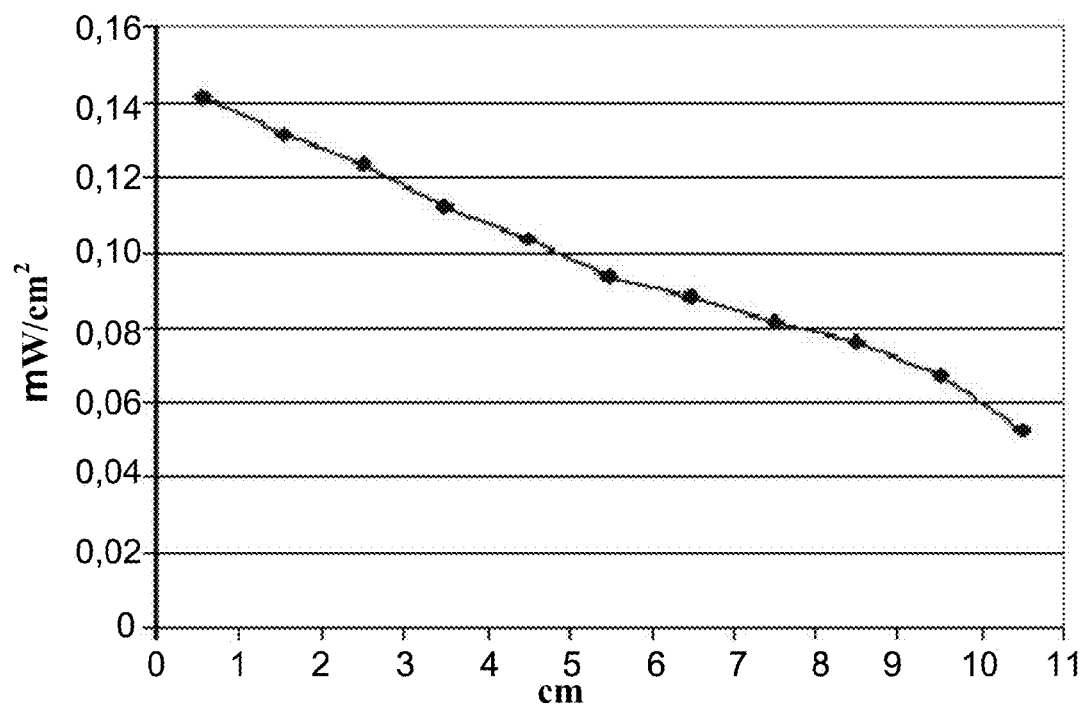
FIG. 2 shows the curve relating to the value of the power generated per unit of surface illuminated, expressed as $mW/cm^2$, in relation to the distance of the cover from the edge of the support containing the solar cell.

It can be seen that, in the absence of edge effects, the average power generated is equal to 0.10 W/cm$^2$ (FIG. 2).

EXAMPLE 3 (COMPARATIVE)

6 g of polymethylmethacrylate Altuglas VSUVT 100 (PMMA) and 49.5 mg of 4,7-di(thien-2'-yl)-2,1,3-benzothiadiazole (DTB) were dissolved in 30 ml of 1,2-dichlorobenzene. The solution obtained was then uniformly deposited on a sheet of polymethylmethacrylate Altuglas VSUVT 100 (PMMA) (dimensions 90×90×6 mm)) using a Doctor Blade-type film applicator and the solvent was left to evaporate at room temperature (25° C.), in a light stream of air, for 24 hours. A red-coloured transparent sheet was obtained (sheet 2), the colour being conferred by the film, whose thickness proved to range from 300 μm to 350 μm.

A photovoltaic cell IXYS-XOD17, having a surface of 1.2 cm$^2$ was then applied to one of the edges of the polymeric sheet.

The main side of the polymeric sheet (that covered by the thin film containing 4,7-di(thien-2'-yl)-2,1,3-benzothiadiazole was then illuminated with a light source having a power of 1 sun (1000 W/m$^2$) and the electric power generated by the effect of the illumination was measured.

The power measurements were carried out by covering, with an opaque coating (cover), surfaces having variable areas of the polymeric support, at an increasing distance from the edge on which the photovoltaic cells were fixed. These measurements under variable screening conditions allow to quantify the contribution of possible waveguide, edge or multiple diffusion effects due to the support and consequently to be subtracted.

Figure 3:
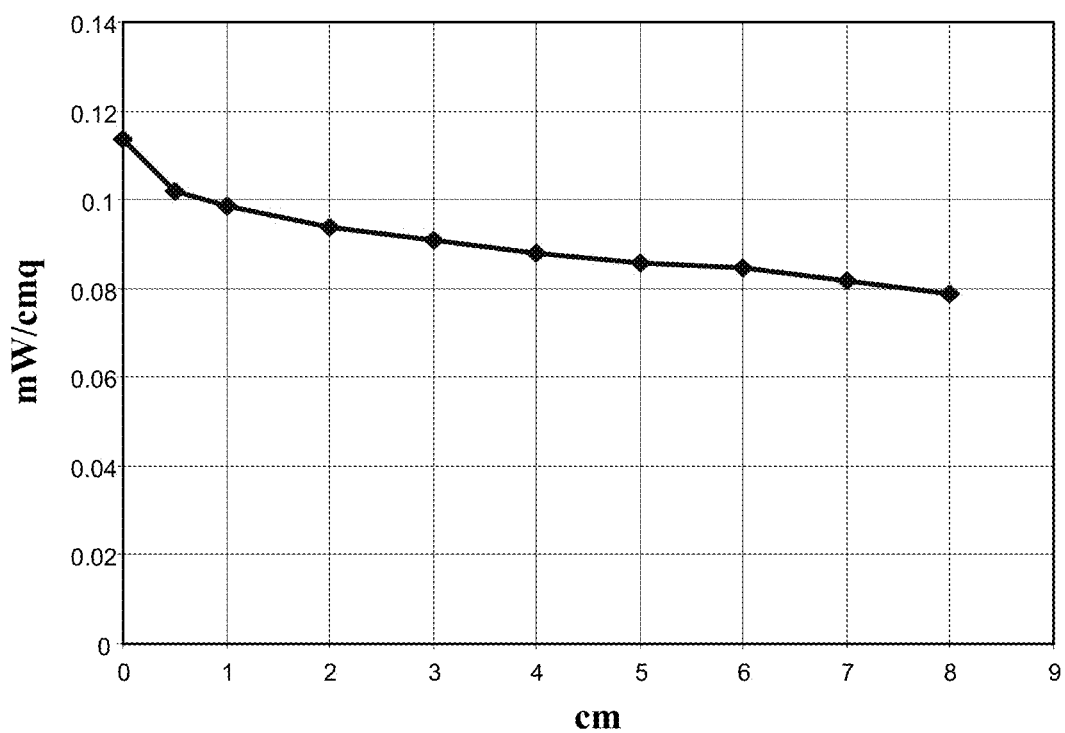
FIG. 3 shows the curve relating to the value of the power generated per unit of surface illuminated, expressed as mW/cm², in relation to the distance of the cover from the edge of the support containing the solar cell.

It can be seen that, in the absence of edge effects, the power generated is fixed at around 0.079 mW/cm$^2$ (FIG. 3) lower than that generated using both 4,7-di(2',2"-bithien-5'-yl)-2,1,3-benzothiadiazole (QTB) (Example 1), and 4,7-di(5"-n-hexyl-2',2"-bithien-5'-yl)-2,1,3-benzothiadiazole (QTB-ex) (Example 2) according to the present invention.

Having described the invention, the following is claimed:

1. A luminescent solar concentrator comprising at least one disubstituted benzothiadiazole compound having general formula (I):

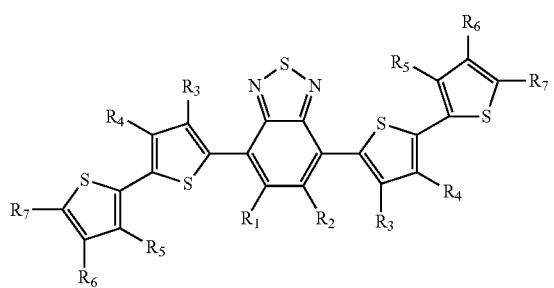

(I)

wherein:
- $R_1$, $R_2$, $R_3$, $R_4$, $R_5$, $R_6$ and $R_7$, equal to or different from each other, represent a hydrogen atom; or they are selected from linear or branched $C_1$-$C_{20}$ alkyl groups, cycloalkyl groups optionally substituted, aryl groups optionally substituted, linear or branched $C_1$-$C_{20}$ alkoxyl groups, optionally substituted;
- or $R_1$ and $R_2$, can be optionally bound to each other so as to form, together with the carbon atoms to which they are bound, a cyclic or a polycyclic system containing from 3 to 14 carbon atoms, saturated, unsaturated, or aromatic, optionally containing one or more heteroatoms selected from the group consisting of oxygen, sulfur, nitrogen, silicon, phosphorous, and selenium;
- or $R_3$ and $R_4$, can be optionally bound to each other so as to form, together with the carbon atoms to which they are bound, a cyclic or a polycyclic system containing from 3 to 14 carbon atoms, saturated, unsaturated, or aromatic, optionally containing one or more heteroatoms selected from the group consisting of oxygen, sulfur, nitrogen, silicon, phosphorous, and selenium;
- or $R_5$ and $R_6$, can be optionally bound to each other so as to form, together with the carbon atoms to which they are bound, a cyclic or a polycyclic system containing from 3 to 14 carbon atoms, saturated, unsaturated, or aromatic, optionally containing one or more heteroatoms selected from the group consisting of oxygen, sulfur, nitrogen, silicon, phosphorous, and selenium;
- or $R_6$ and $R_7$, can be optionally bound to each other so as to form, together with the carbon atoms to which they are bound, a cyclic or a polycyclic system containing from 3 to 14 carbon atoms, saturated, unsaturated, or aromatic, optionally containing one or more heteroatoms selected from the group consisting of oxygen, sulfur, nitrogen, silicon, phosphorous, and selenium.

2. The luminescent solar concentrator according to claim 1, wherein in said general formula (I), the substituents $R_1$, $R_2$, $R_3$, $R_4$, $R_5$, $R_6$ and $R_7$, represent a hydrogen atom.

3. The luminescent solar concentrator according to claim 1, wherein in said general formula (I), the substituents $R_1$, $R_2$, $R_3$, $R_4$, $R_5$ and $R_6$, represent a hydrogen atom, the substituent $R_7$ represents a hexyl group.

4. A photovoltaic device selected from photovoltaic cells, photovoltaic modules, solar cells, or solar modules, on both rigid and flexible supports, comprising a luminescent solar concentrator (LSC) that includes at least one disubstituted benzothiadiazole compound having general formula (I), according to claim 1.

* * * * *